(12) United States Patent
Blakesley et al.

(10) Patent No.: US 6,750,059 B1
(45) Date of Patent: Jun. 15, 2004

(54) ARCHIVING OF VECTORS

(75) Inventors: Robert W. Blakesley, Frederick, MD (US); Mindy D. Goldsborough, Gaithersburg, MD (US)

(73) Assignee: Whatman, Inc., Newton, MA (US)

( * ) Notice: Subject to any disclaimer, the term of this patent is extended or adjusted under 35 U.S.C. 154(b) by 0 days.

(21) Appl. No.: 09/354,664

(22) Filed: Jul. 16, 1999

Related U.S. Application Data

(60) Provisional application No. 60/093,073, filed on Jul. 16, 1998, and provisional application No. 60/100,737, filed on Sep. 17, 1998.

(51) Int. Cl.$^7$ .................. C12N 15/64; C12N 15/74; G01N 33/48
(52) U.S. Cl. .................. 435/471; 435/40.5; 435/320.1
(58) Field of Search .............................. 435/40.5, 91.2, 435/471, 320.1

(56) References Cited

U.S. PATENT DOCUMENTS

| | | |
|---|---|---|
| 4,483,920 A | 11/1984 | Gillespie et al. |
| 4,833,239 A | 5/1989 | DeBonville et al. |
| 4,997,932 A | 3/1991 | Reardon et al. |
| 5,047,345 A | 9/1991 | DeBonville et al. |
| 5,187,083 A | 2/1993 | Mullis |
| 5,234,809 A | 8/1993 | Boom et al. |
| 5,234,824 A | 8/1993 | Mullis |
| 5,438,128 A | 8/1995 | Nieuwkerk et al. |
| 5,496,562 A | 3/1996 | Burgoyne ............... 424/488 |
| 5,652,141 A | 7/1997 | Henco et al. ............ 435/270 |
| 5,658,548 A | 8/1997 | Padhye et al. ........... 423/335 |
| 5,756,126 A | 5/1998 | Burgoyne ............... 424/488 |
| 5,804,684 A | 9/1998 | Su |
| 5,807,527 A | 9/1998 | Burgoyne ............... 422/488 |
| 5,989,431 A | 11/1999 | Evans et al. |
| 6,027,750 A | 2/2000 | Gautsch et al. |

FOREIGN PATENT DOCUMENTS

| | | |
|---|---|---|
| WO | WO 96/39813 | 12/1996 |
| WO | WO 99/13976 | 3/1999 |
| WO | WO 99/16869 | 4/1999 |
| WO | WO 99/38962 | 8/1999 |
| WO | WO 99/39009 | 8/1999 |
| WO | WO 99/39010 | 8/1999 |
| WO | WO 00/40697 | 7/2000 |

OTHER PUBLICATIONS

Hanahan Studies on transformation of *Escherichia coli* with plasmids. J. Mol. Biol. vol. 166 pp. 557–580, 1983.*
Smith et al, Biolistic transformation of prokaryotes: factor that affect biolistic transformation of very small cells, 1992, Journal of General Microbiology, vol./No. 138, pp. 239–248.*
Natarajan P, Trinh T, Mertz L, Goldsborough M, Fox DK. , Paper–based archiving of mammalian and plant samples for RNA analysis. Biotechniques. 29(6): pp. 1328–1333 (2000).
English language abstract of JP 62–104581, Dialog Accession No. JP362104581A. May 15, 1987.
English language abstract of DE 4333805, Dialog Accession No. DE004333805A1. Mar. 2, 1995.
Enlgish language abstract of WO 96/08500, Mar. 26, 1996.
Gentra Systems, "Generation™ Capture Column™ Kit: Technical Report," Minneapolis, MN (Oct. 1997).
Rogers, C., and Burgoyne, L., "Bacterial Typing: Storing and Processing of Stabilized Reference Bacteria for Polymerase Chain Reaction without Preparing DNA—An Example of an Automatable Procedure," *Anal. Biochem.* 247:223–227 (May 1997).

* cited by examiner

*Primary Examiner*—John S. Brusca
(74) *Attorney, Agent, or Firm*—Edwards & Angell, LLP

(57) ABSTRACT

The invention relates to a solid medium or matrix for storage of nucleic acid molecules (e.g. RNA and/or DNA), particularly vectors and especially plasmids, comprising a solid matrix preferably having a compound or composition which protects against degradation of nucleic acids incorporated into or absorbed on the matrix. The invention also relates to methods for storage or isolation/purification of nucleic acids using this solid medium, and in situ use of the stored or isolated/purified nucleic acids.

20 Claims, 3 Drawing Sheets

Amplification of Bacterial Plasmids from FTA

ARCHIVING OF VECTORS

CROSS REFERENCE TO RELATED APPLICATIONS

The present application claims the benefit of the filing dates of U.S. application Ser. No. 60/093,073, filed Jul. 16, 1998, and Ser. No. 60/100,737, filed Sep. 17, 1998, the disclosures of which are incorporated by reference herein in their entireties.

BACKGROUND AND SUMMARY OF THE INVENTION

The present invention relates to a solid medium or support for use in the storage (preferably the long term storage) of nucleic acids (e.g. DNA and RNA, ribosomal RNA and messenger RNA), particularly one or more vectors and especially one or more plasmids, and to methods which comprise the use of this solid medium or support. In particular, the invention relates to a method for storage and transport of such nucleic acids or vectors on the solid medium, as well as to methods which involve either recovery or purification of the nucleic acids or vectors from the solid medium, or the use or manipulation of the nucleic acids or vectors obtained from or contained by or on the solid medium. Such use or manipulation includes, for example, digestion (e.g. with one or more nucleases, exonucleases or endonucleases such as restriction enzymes), synthesis (e.g. with one or more polymerases and/or reverse transcriptases), amplification (e.g. by polymerase chain reaction with one or more polymerases), sequencing (e.g. with one or more polymerases), or transformation or transfection into one or more host cells using, for example, chemically competent or electrocompetent cells or using known transfection reagents and techniques. The preferred medium or support is a matrix which protects against degradation of nucleic acid incorporated onto the matrix. Such a matrix may comprise an absorbent cellulose-based matrix or paper, or a micromesh of synthetic plastic material such as those described in U.S. Pat. No. 5,496,562, which is incorporated by reference herein. Preferably, the matrix comprises a composition comprising a weak base, a chelating agent, an anionic surfactant or anionic detergent, and optionally uric acid or a urate salt, wherein said composition is absorbed on or incorporated into said matrix. FTA™ paper brand cellulose base solid matrix and derivatives, variants and modifications thereof are included among such supports.

Another aspect of the invention relates to such a solid medium or support for use in the sampling, purifying and/or analyzing of one or more non-chromosomal DNA (e.g. mitochondria, chloroplast, F') and to methods which comprise the use of this solid medium or support for such purposes.

For many projects, generation of numerous DNA samples from biological specimens is routine. Handling and archiving a large collection can become a logistical problem for the laboratory. One solution, used in forensic labs, is the blood-storage medium cellulose based solid matrix paper card, such as an FTA™ Card. A cellulose based solid matrix paper card stores genomic DNA in the form of dried spots of human whole blood, the cells of which were lysed when they contacted the paper. Stored at room temperature, genomic DNA on a cellulose based solid matrix paper is reported to be stable, e.g., for at least 7.5 years using an FTA™ Card brand cellulose based solid matrix (Burgoyne, et al., "Conventional DNA Collection and Processing: Disposable Toothbrushes and FTA™ Paper as a Non-threating Buccal-Cell Collection Kit Compatible with Automatable DNA Processing," 8th *International Symposium on Human Identification*, (Sep. 17–20, 1997). Before analysis of the captured DNA, a few simple washing steps remove the stabilizing chemicals and cellular inhibitors of enzymatic reactions. Since the DNA remains with the paper, the manipulations to purify the DNA are simplified and amenable to automation. DNA samples on cellulose based solid matrix cards offer a very compact archival system compared to glass vials or plastic tubes located in precious freezer space.

Bacterial DNAs spotted on cellulose based solid matrix cards may be an efficient system for storage and retrieval as well. Recently, Rogers and Burgoyne characterized by PCR-ribotyping culture samples of several bacterial strains of Staphylococcus and *E. coli* stored on FTA™ Cards brand cellulose based solid matrix (Rogers, et al., (1997) *Anal. Biochem.* 247:223). Further, purified plasmid DNA was efficiently recovered after spotting on treated paper, however, encasement of the paper in polystyrene was used for storage (Burgoyne, U.S. Pat. No. 5,496,562, which is incorporated by reference herein).

According to the present invention, any nucleic acids (e.g. RNA and DNA and particularly RNA and DNA vectors) may be archived and later recovered and/or manipulated by a simple and efficient method in which the host carrying the one or more nucleic acids or vectors are contacted with a solid medium (preferably FTA™ paper brand cellulose based solid matrix, or derivatives, variants or modifications thereof), without the need to encase the support or use protective coatings (such as polystyrene) to store the nucleic acids or vectors. Thus, the invention avoids the need to use organic solvents or harsh chemicals to remove such protective coatings before use, manipulation, purification or isolation of the nucleic acid molecules or vectors can take place. In another aspect, purified nucleic acid molecules or vectors may be used, although in a preferred aspect, crude preparations (unpurified vector preparations) containing the one or more nucleic acid molecules or vectors may be contacted with the solid medium or support. Thus, the invention provides methods to isolate and/or purify nucleic acid molecules or vectors from any sample containing one or more vectors such as host cells, viruses, viral plaques, and/or crude preparations from biological materials (such as host cell or virus extracts, lysates, debri, hydrolysates, and the like). Such isolated and/or purified nucleic acid molecules or vectors obtained from or contained by the solid support or matrix may be used or manipulated in one or more standard molecular biology techniques, such as digestion, sequencing, amplification, synthesis and transformation/transfection reactions. In a particularly preferred aspect, one or more host cells containing the nucleic acid molecules or vectors to be isolated, stored and/or manipulated can be contacted directly with the medium or support. According to the present invention, host cell cultures or colonies from plates may be used. Preferred host cells for use in the invention include prokaryotic or eukaryotic host cells, particularly gram positive and gram negative bacteria such as Escherichia, Streptomyces, Pseudomonas, and the like.

Other preferred embodiments of the present invention will be apparent to one of ordinary skill in light of what is known in the art, in light of the following drawings and description of the invention, and in light of the claims.

DETAILED DESCRIPTION OF THE INVENTION

Figure 1:
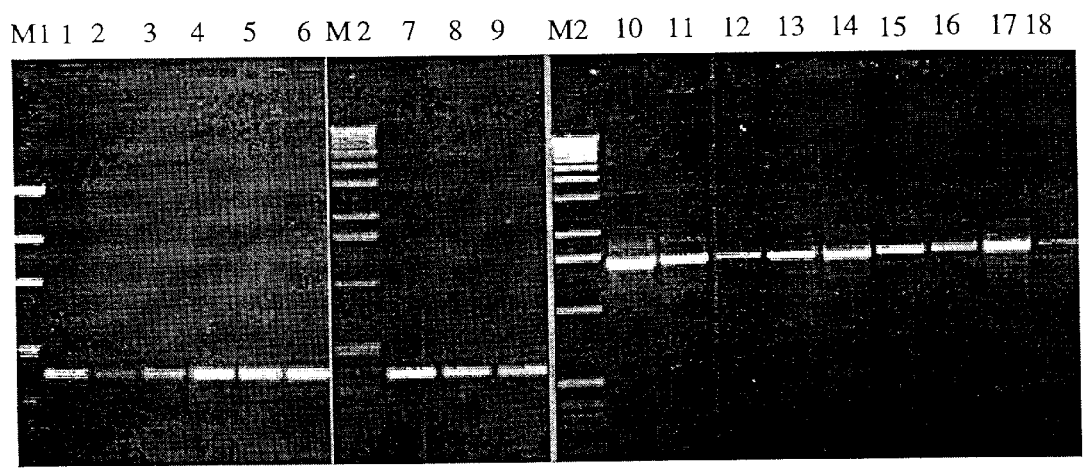
FIG. 1 is a PCR analysis of bacterial genomic DNA on an FTA™ Card. The agarose gel analysis of the amplification products pictured are shown as follows: lanes 1–3: *Agrobacter tumefaciens* strain LBA4404; lanes 4–6: *Agrobacter tumefaciens* strain EHA101; lanes 7–9: *E coli* DH10B strain; lanes 10–12: *Streptomyces coelicolor*; lanes 13–15: *S. lividans*; and lanes 16–18: *S. paralus*. Molecular size standards are a Low DNA Mass™ Ladder (M1) and a 1 Kb DNA Ladder (M2).

In the description that follows, a number of terms used in the fields of molecular biology and recombinant DNA technology are utilized extensively. In order to provide a clearer and consistent understanding of the specification and claims, including the scope to be given such terms, the following definitions are provided.

Amplification. As used herein, "amplification" refers to any in vitro method for increasing the number of copies of a nucleotide sequence with the use of a polymerase. Nucleic acid amplification results in the incorporation of nucleotides into a nucleic acid (e.g., DNA) molecule or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR). One PCR reaction may consist of 5 to 100 "cycles" of denaturation and synthesis of a nucleic acid molecule.

Polymerases (including DNA polymerases and RNA polymerases) useful in accordance with the present invention include, but are not limited to, *Thermus thermophilus* (*Tth*) DNA polymerase, *Thermus aquaticus* (*Taq*) DNA polymerase, *Thermologa neopolitana* (*Tne*) DNA polymerase, *Thermotoga maritima* (*Tma*) DNA polymerase, *Thermococcus litoralis* (*Tli* or VENT™) DNA polymerase, *Pyrococcus furiosus* (*Pfu*) DNA polymerase, DEEPVENT™ DNA polymerase, *Pyrococcus woosii* (*Pwo*) DNA polymerase, *Bacillus sterothermophilus* (*Bst*) DNA polymerase, *Bacillus caldophilus* (*Bca*) DNA polymerase, *Sulfolobus acidocaldarius* (*Sac*) DNA polymerase, *Thermoplasma acidophilum* (*Tac*) DNA polymerase, *Thermus flavus* (*Tfl/Tub*) DNA polymerase, *Thermus ruber* (*Tru*) DNA polymerase, *Thermus brockianus* (DYNAZYME™) DNA polymerase, *Methanobacterium thermoautotrophicum* (*Mth*) DNA polymerase, mycobacterium DNA polymerase (*Mtb, Mlep*), and mutants, and variants and derivatives thereof. RNA polymerases such as T3, T5 and SP6 and mutants, variants and derivatives thereof may also be used in accordance with the invention.

Polymerases used in accordance with the invention may be any enzyme that can synthesize a nucleic acid molecule from a nucleic acid template, typically in the 5' to 3' direction. The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include *Taq, Tne, Tma, Pfu, Tfl, Tth*, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J.-M, et al., *Nucl. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3' exonuclease activity) are typically used. See U.S. Pat. No. 5,436,149; and U.S. Pat. No. 5,512,462; Barnes, W. M., *Gene* 112:29–35 (1992), the disclosures of which are incorporated herein in their entireties. Examples of DNA polymerases substantially lacking in 3' exonuclease activity include, but are not limited to, *Taq, Tne*(exo⁻), *Tma*(exo⁻), *Pfu*(exo⁻), *Pwo*(exo⁻) and *Tth* DNA polymerases, and mutants, variants and derivatives thereof.

Host. Any prokaryotic or eukaryotic cell that is the recipient of a replicable expression vector or cloning vector. The terms "host" or "host cell" may be used interchangeably herein. For examples of such hosts, see Maniatis et al., *Molecular Cloning: A Laboratory Manual*, Cold Spring Harbor Laboratory, Cold Spring Harbor, N.Y. (1982). Preferred prokaryotic hosts include, but are not limited to, bacteria of the genus Escherichia (e.g. *E. coli*), Bacillus, Staphylococcus, Agrobacter (e.g. *A. tumefaciens*), Streptomyces, Pseudomonas, Salmonella, Serratia, Caryophanon, etc. The most preferred prokaryotic host is *E. coli*. Bacterial hosts of particular interest in the present invention include *E. coli* K12, DH10B, DH5α and HB101. Preferred eukaryotic hosts include, but are not limited to, fungi, fish cells, yeast cells, plant cells and animal cells. Particularly preferred animal cells are insect cells such as Drosophila cells, Spodoptera Sf9 and Sf21 cells and Trichoplusa High-Five cells; nematode cells such as *C. elegans* cells; and mammalian cells such as COS cells, CHO cells, VERO cells, 293 cells, PERC6 cells, BHK cells and human cells.

Vector. A vector is a nucleic acid molecule (preferably DNA) capable of replicating autonomously in a host cell. Such vectors may also be characterized by having a small number of endonuclease restriction sites at which such sequences may be cut without loss of an essential biological function and into which nucleic acid molecules may be spliced to bring about its replication and cloning. Examples include plasmids, autonomously replicating sequences (ARS), centromeres, cosmids and phagemids. Vectors can further provide primer sites, e.g., for PCR, transcriptional and/or translational initiation and/or regulation sites, recombinational signals, replicons, etc. The vector can further contain one or more selectable markers suitable for use in the identification of cells transformed or transfected with the vector, such as kanamycin, tetracycline, amplicillin, etc.

In accordance with the invention, any vector may be used. In particular, vectors known in the art and those commercially available (and variants or derivatives thereof) may be used in accordance with the invention. Such vectors may be obtained from, for example, Vector Laboratories Inc., InVitrogen, Promega, Novagen, NEB, Clontech, Boehringer Mannheim, Pharmacia, EpiCenter, OriGenes Technologies Inc., Stratagene, Perkin Elmer, Pharmingen, Life Technologies, Inc., and Research Genetics. Such vectors may then for example be used for cloning or subcloning nucleic acid molecules of interest. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like.

Other vectors of interest include viral origin vectors (M13 vectors, bacterial phage λ vectors, baculovirus vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8).

Particular vectors of interest include prokaryotic expression vectors such as pcDNA II, pSL301, pSE280, pSE380, pSE420, pTrcHisA, B, and C, pRSET A, B, and C (Invitrogen, Inc.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Life Technologies, Inc.) and variants and derivatives thereof. Vectors can also be eukaryotic expression vectors such as pFastBac, pFastBac HT, pFast-Bac DUAL, pSFV, and pTet-Splice (Life Technologies, Inc.), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Phannacia, Inc.), p3'SS, pXT1, pSG5, pPbac, pMbac, pMC1neo, and pOG44 (Stratagene, Inc.), and pYES2, pAC360, pBlueBacHisA, B, and C, pVL1392, pBsueBacIII, pCDM8, pcDNA1, pZeoSV, pcDNA3 pREP4, pCEP4, and pEBVHis (Invitrogen, Inc.) and variants or derivatives thereof.

Other vectors of particular interest include pUC18, pUC19, pBlueScript, pSPORT, cosmids, phagemids, fosmids (pFOS1), YAC's (yeast artificial chromosomes), BAC's (bacterial artificial chromosomes), pBAC108L, pBACe3.6, pBeloBAC11 (Research Genetics), PACs, P1 (*E. coli* phage), pQE70, pQE60, pQE9 (Qiagen), pBS vectors, PhageScript vectors, BlueScript vectors, pNH8A, pNH16A, pNH18A, pNH46A (Stratagene), pcDNA3 (InVitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0, pSV-SPORT1 (Life Technologies, Inc.), and the vectors described in Provisional Patent Application No. 60/065,930, filed Oct. 24, 1997, the entire contents of which is herein incorporated by reference, and variants or derivatives thereof.

Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZα, pGAPZ, pGAPZα, pBlueBac4.5, pBlueBacHis2, pMelBac, pSinRep5, pSinHis, pIND, pIND(SP1), pVgRXR, pcDNA2.1. pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe,SV2, pRc/CMV2, pRc/RSV, pREP4, pREP7, pREP8, pREP9, pREP10, pCEP4, pEBVHis, pCR3.1, pCR2.1, pCR3.1-Uni, and pCRBac from Invitrogen; λExCell, λgt11, pTrc99A, pKK223-3, pGEX-1λT, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32 LIC, pET-30 LIC, pBAC-2cp LIC, pBACgus-2cp LIC, pT7Blue-2 LIC, pT7Blue-2, kSCREEN-1, λBlueSTAR, pET-3abcd, pET-7abc, pET9abcd, pET11abcd, pET12abc, pET-14b, pET-15b, pET-16b, pET-17b- pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, βpgal-Control, pβgal-Promoter, pβgal-Enhancer, pCMVβ, pTet-Off, pTet-On, pTK-Hyg, pRetro-Off, pRetro-On, pIRESIneo, pIRES1hyg, pLXSN, pLNCX, pLAPSN, pMAMneo, pMAMneo-CAT, pMAMneo-LUC, pPUR, pSV2neo, pYEX 4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pWE15, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOP13 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene, and derivatives or variants thereof.

Two-hybrid and reverse two-hybrid vectors of particular interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4–5, pNLexA, pYESTrp and variants or derivatives thereof.

Storage. As used herein, "storage" refers to maintaining the support/vectors for a period of time at a temperature or temperatures of interest. Preferably, storage is accomplished at about 20 to 30° C. (preferably room temperature, e.g. 25° C.), but may be at higher or lower temperatures depending on the need. Lower storage temperatures may range from about 0 to 20° C., −20 to 0° C., and −80 to −20° C. Long term storage in accordance with the invention is greater than one year, preferably greater than 2 years, still more preferably greater than 3 years, still more preferably greater than 5 years, still more preferably greater than 10 years, and most preferably greater than 15 years.

Other terms used in the fields of recombinant DNA technology and molecular and cell biology as used herein will be generally understood by one of ordinary sill in the applicable arts.

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

All reagents were from Life Technologies, Inc., Rockville, Md., unless otherwise noted. The cellulose based solid matrix used was an FTA™ paper or FTA™ Card brand cellulose based solid matrix, unless otherwise noted.

Example 1

Preparation of Samples on an FTA™ Card brand cellulose based solid matrix. From bacterial cultures grown overnight, 5 µl were spotted in separate locations on an FTA™ Card brand cellulose based solid matrix (Cat. No. 10786) and allowed to dry overnight at room temperature. Bacterial colonies from petri dishes were spotted onto an FTA™ Card brand cellulose based solid matrix, suspending a colony in 5 µl of PBS, applying the entire volume as a single spot, then allowing the paper to dry overnight at room temperature.

Using a HARRIS MICRO PUNCH™ Apparatus with mat, a 2-mm punch was taken from a dried bacterial or yeast spot (~6 mm diameter), then washed with FTA™ Purification Reagent (Cat. No. 10876) and TE buffer according to manufacturer's recommendations. The washed punch was air dried for 1 hour at room temperature or 30 min at 60° C.

Processed cellulose based solid matrix card punches were either assayed immediately or stored at 4° C.

Amplification. DNA was amplified directly from a washed FTA™ Card punch placed in 50 µl of 1×PCR buffer, 1.5 mM Mg$^{++}$, 0.2 µM dNTPs, 1.25 units Platinum™ *Taq* DNA Polymerase, and 0.2 µM primers (Table 1). For *Agrobacter tumefaciens* genomic sequence, amplification was: one cycle of 94° C. for 1 min, 30 cycles of 94° C. for 1 min., 55° C. for 30 s, 72° C. for 3 min and one cycle of 72° C. for 10 min. For *E. coli* DH10B™ genomic DNA and Streptomyces samples, amplification was: one cycle of 94° C. for 1 min, 36 cycles of 94° C. for 30 s, 55° C. for 1 min, 72° C. for 1 min, and one cycle of 72° C. for 10 min.

TABLE 1

Primer sequences

| Target | Amplicon | Size (bp) | Primer Sequence |
|---|---|---|---|
| *Agrobacter tumefaciens* | 16S rRNA | 284 | GGGAA AGATT TATCG GGGAT G GGCTG CTGGC ACGAA GTTA (SEQ ID NO:1) |
| *E. coli* DH10B cells | rrsE | 372 | CTGAG ACACG GTCCA GACTC CTACG TCACC GCTAC ACCTG GGATT CTACC (SEQ ID NO:2) |
| Streptomyces | 16S rRNA | 1500 | AGAGT TTGAT GATCC TGGCT CAG AAGGA GGTGA TCCAG CCGCA (SEQ ID NO:3) |
| Plasmid | pSUsrmB2 | 1503 | CCCAG TCACG ACGTT GTAAA ACG AGCGG ATAAC AATTT CACAC AGG (SEQ ID NO:4) |
| Plasmid | pMAB32 | 1800 | GAATA AGTGC GACAT CATCA TC GTAAA TTTCT GGCAA GGTAG AC (SEQ ID NO:5) |
| Plasmid | pJH11104 | 1200 | ACTTC TTCGC CCCCG TTTTC GCTGA CTTGA CGGGA CGGCG (SEQ ID NO:6) |

For yeast genomic DNA and yeast plasmid (two-hybrid) DNAs, plates were obtained which had several colonies of each 2 two-hybrid (ProQuest, Cat. No. 10835-023) control strain. From each plate, several individual colonies were taken. Each individual colony was suspended in 5 µl PBS and each 5 µl aliquot was spotted in individual spots onto an FTA™ Card brand cellulose based solid matrix.

Plasmids pSUsrmB2 and pJH11104 were amplified in the same reaction mixture described above. Amplification of pMAB32 was in a reaction mixture using eLONGase™ Amplification System at 1.5 mm Mg$^{++}$. For all three plasmids, the incubation profile was one cycle of 94° C. for 1 min, one cycle of 94° C. for 15 s, and 30 cycles of 94° C. for 15 s, 55° C. for 30 s, 72° C. for 3 min.

For yeast (*Saccharomyces cerevisiae*) plasmid and genomic amplifications, reaction conditions using eLONGase™ Amplification System were: one cycle of 94° C. for 2 min, 40 cycles of 94° C. for 15 s, 55° C. for 20 s, 72° C. for 5 min. Primer sequences used for yeast amplification are shown in Table 2.

TABLE 2

Primer sequences

| Target | Amplicon | Size(bp) | Primer Sequence |
|---|---|---|---|
| Plasmid | pPC97 | 255 | |
| Plasmid | pPC97-RB | 2088 | |

TABLE 2-continued

Primer sequences

| Target | | Amplicon Size(bp) | Primer Sequence |
|---|---|---|---|
| Plasmid | pPC97-dE2F | 834 | GAATA AGTGC GACAT CATCA TC GTAAA TTTCT GGCAA GGTAG AC (SEQ ID NO:5) |
| Plasmid | pPC97-Fos | 447 | |
| Plasmid | pCL1 | 2853 | |
| Saccharomyces cerevisiae MaV203(MATa) | SPAL promoter | 350 | GCGAG GCATA TTTAT GGTGA AGG CATTT CCGTG CAAAG GTACT AAC (SEQ ID NO:7) |

Aliquots of each reaction product were analyzed by electrophoresis in a 1.5% (w/v) agarose/TAE gel.

Transformation. Cells were transformed with plasmid DNA from washed FTA™ Card brand cellulose based solid matrix, punches, either by adding a punch directly to the reaction or by adding 5 µl of a TE buffer extract, which had soaked the punch for 20 min. at room temperature. Both MAX Efficiency DH5α™ and MAX Efficiency DH10B cells were transformed according to manufacturer's recommendations. Various dilutions of the final 1-ml transformation reaction volume (100 µl of a 1/100 dilution, 100 µl of a 1/10 dilution, 100 µl of undiluted cells, and 10 µl of undiluted cells) were plated on the appropriate media and incubated overnight at 37° C.

Using samples from overnight liquid cultures spotted on FTA™ Cards brand cellulose based solid matrix, Rogers, and Burgoyne generated the expected diagnostic PCR patterns for each of six bacterial strains tested (Rogers, et al., (1997) Anal. Biochem. 247:223). However, according to the present invention, bacterial colonies placed on an FTA™ Card brand cellulose based solid matrix, were tested. Unlike Rogers and Burgoyne who tested two complex methods of processing, all bacteria-spotted FTA™ Cards brand cellulose based solid matrix, in this study were processed with simple washes.

Bacterial genomic DNA targets amplified directly from washed punches gave the expected bands (FIG. 1). FTA™ Cards brand cellulose based solid matrix were useful for screening and identifying colonies of Agrobacter bacterium from plants, a gram negative E. coli bacterium, and a difficult-to-lyse, gram-positive Streptomyces bacterium. Success was due in part to the robust nature of the amplification reaction, not requiring quantitation of the DNA beforehand. Liquid cultures of the same bacteria spotted on the cellulose based solid matrix card, such as an FTA™ Card, may also work as well as the colonies. Also, transfer of bacteria by colony lift from the solid growth medium surface with an appropriate-sized cellulose based solid matrix card may be used. Consistent with the known properties of at least one brand cellulose based solid matrix (i.e., an FTA™ Card), bacteria could not be rescued after washed, bacteria-spotted punches were placed on solid growth media and incubated for >3 days.

Figure 2:
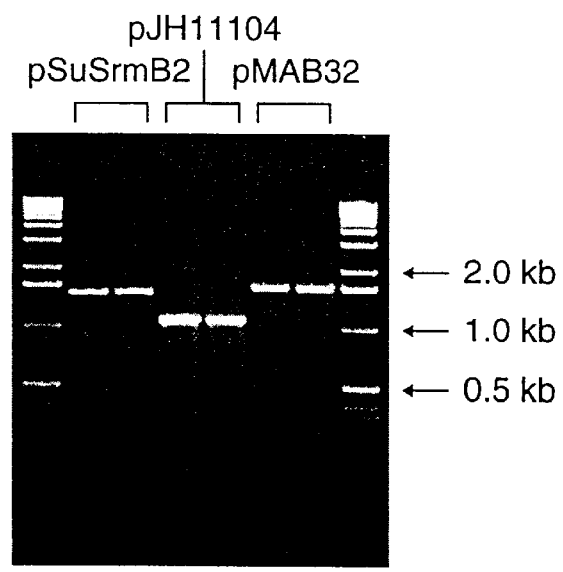
FIG. 2 is a PCR analysis of plasmid DNA from *E. coli* (DH10B) on an FTA™ Card.
Figure 3:
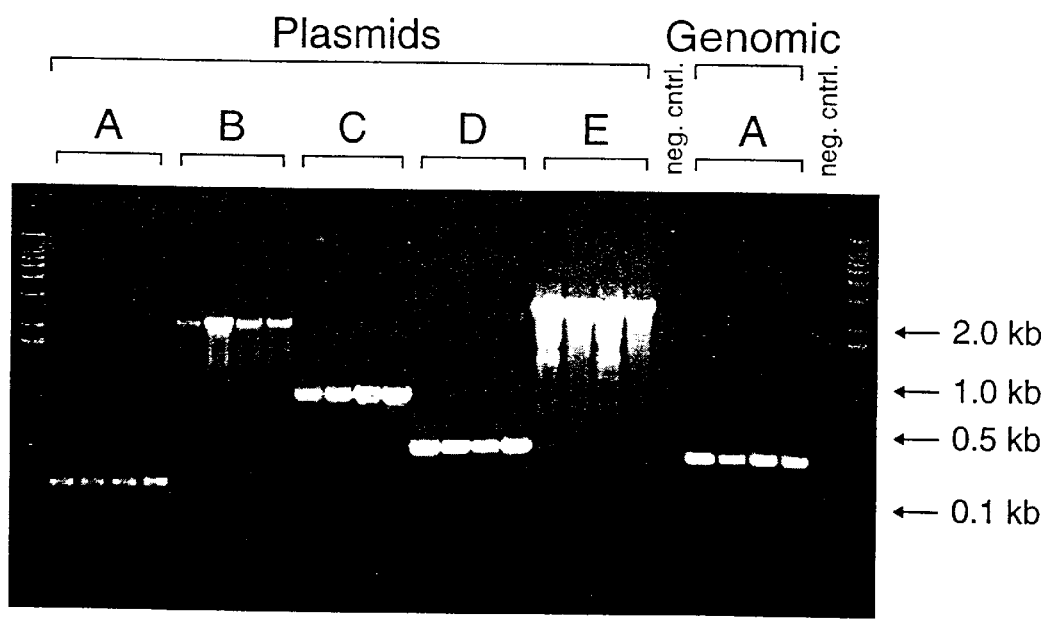
FIG. 3 is a PCR analysis of plasmid and genomic DNA from *Saccharomyces cerevisiae* on an FTA™ Card.

Retention of plasmid DNA on FTA™ Cards brand cellulose based solid matrix was tested. Burgoyne reported that purified plasmid DNA spotted on treated paper was efficiently removed with TE buffer (after treatment with organic solvents to remove polystyrene protection coating) as measured by PCR and transformation (Burgoyne, U.S. Pat. No. 5,496,562). However, using purified DNA did not employ the advantage of directly spotting plasmid-containing-bacteria on a cellulose based solid matrix card. Three cultures of E. Coli were spotted onto an FTA™ Card brand cellulose based solid matrix and processed punches were amplified. Plasmid DNA was retained on the cellulose based solid matrix card as the expected amplicons were observed (FIG. 2). However, the amount of plasmid DNA remaining with the paper is probably low. Standard fluorescent cycle sequencing of plasmid DNA directly from a washed punch did not detect any signal (data not shown) even though plasmid DNA in a single colony has been shown to be sufficient for cycle sequencing (Young, A. and Blakesley, R. (1991) Focus 13, 137). However, sequencing of the plasmid DNA could be accomplished after the plasmid DNA was initially amplified as described above. Moreover, sequencing may be accomplished directly from the FTA™ brand cellulose based solid matrix sample under appropriate conditions which allow sufficient amounts of plasmid DNA to be retained on FTA™ paper brand cellulose based solid matrix.

Although some plasmid DNA remained with the FTA™ Card brand cellulose based solid matrix through an extensive wash procedure, it is probable the DNA is loosely associated and some of it releases during each wash. This was confirmed by generation of the correct amplicon when a 5 µl TE buffer extraction of a washed punch was amplified by PCR (data not shown). This result suggested that the released plasmid DNA from washed punches might also be recovered by biological amplification, i.e., bacterial transformation. DH5α and DH10B cells were each successfully transformed with 5 µl from a TE-buffer extraction of a washed punch previously spotted with bacteria harboring one of three plasmids (data not shown). Successful rescue of the three plasmids led to testing a washed punch introduced directly into the cell transformation reaction (Table 3). Transformation reactions tested (two cell types and two DNA introduction methods) gave comparable results (data not shown). In all cases, bacterial clones were easily recovered, making cellulose based solid matrix cards, such as FTA™ Cards brand cellulose based solid matrix, potentially very convenient and cost effective for the long term storage of bacterial clones. Similarly, other bacterial clones harboring DNAs, such as cosmids, BACs or PACs, can be recovered from samples archived on these cellulose based solid matrix cards.

TABLE 3

Transformation of DH5α cells with plasmids
on an FTA ™ card punch

| Plasmid | Size (kb) | Copy Number | Transformants/punch |
|---|---|---|---|
| pSUsrmB2 | 5.3 | 6–10 | 7,000 |
| pJH11104 | 2.7 | ~100 | 28,000 |
| pMAB32 | 11.2 | >100 | 5,700 |

Results are the average from 4 dilutions.

Example 2

In an effort to streamline the process required to utilize cellulose based solid matrix cards for the archiving of vectors, further studies on the transformation of competent cells with plasmid DNA on FTA™ Cards brand cellulose based solid matrix were undertaken. An overnight culture of bacterial host cells (DH5α) containing the pSUsrmB2 plasmid were spotted onto FTA™ Cards brand cellulose based solid matrix. It was believed that the processing step of the FTA™ protocol could be optimized for samples that do not contain blood (examples of such samples are bacterial cells, tissue culture cells, buccal swabs, concentrates of certain body fluids such as saliva or urine, etc.). The FTA™ Processing Reagent was initially designed to purify the DNA from blood samples spotted onto FTA™ Cards. This reagent is required for optimal purification of blood samples when enzyme-based assays are utilized to remove heme and other enzymatic inhibitors.

Modified processing protocols were tested for application in PCR by processing punches in a specific manner and then attempting to amplify the plasmid DNA on the punch using PCR primers (see Table 1) specific for pSUsrmB2 plasmid DNA. Punches were either not processed in any way, processed according to the manufacturer's directions using three 5 minute soaks in FTA™ brand cellulose based solid matrix Processing Reagent followed by two 5 minute soaks in TE, or processed using two abbreviated TE rinses. TE was chosen as it is a commonly used biological buffer readily available in the laboratory, although any solutions or buffer systems (e.g. PBS, TAE, TBE, Hepes, Ringers solution, Dulbecco's Phosphate buffered saline, Earle's balanced salt solution, Gey's balanced salt solution, Hank's balanced salt solution, etc., see Life Technologies catalogue) or even water may be used in this modified processing method. Preferably, solutions which do not destroy or degrade nucleic acid molecules are used. Amplification was not obtained with punches were unprocessed, but that punches receiving two brief washes with TE amplified to the same level as those processed using the full protocol. It is not unexpected that the unprocessed FTA™ brand cellulose based solid matrix punch would not produce amplification products since the reagents on the unprocessed paper would be expected to render the polymerase inactive.

The above results were obtained with standard PCR methodologies that are generally not useful for analysis of the relative amounts of DNA in any given sample. To determine if there was a difference in the amount of DNA being retained on the filter with the different processing procedures, quantitative PCR using the Perkin Elmer 7700 TaqMan machine was performed. Punch samples (2 mm) were removed from FTA™ Cards brand cellulose based solid matrix that contained spots of HeLa cells ($5 \times 10^7$ cells/ml) dried onto the paper surface. These punches were processed using either the full protocol or the abbreviated TE washes then subjected to amplification using the Perkin Elmer b-actin probe and primers in the TaqMan PCR Reagent Kit (Cat. No. N808-0230, PE Applied Biosystems, Foster City, Calif.). The signal from the cellulose based solid matrix card punches processed using 2 TE washes was consistently about 2-fold higher than the signal from cellulose based solid matrix card punches that were processed using the manufacturer's directions.

To test streamlining of the processing steps for transformation of plasmid DNA, 2 mm punches were taken from the FTA™ Cards brand cellulose based solid matrix containing overnight cultures of pSUsrrnB2 and processed in different manners prior to transformation of competent DH5α cells. Punches were processed either according to the manufacturer's directions, or processed using two abbreviated rinses of TE, or used unprocessed, directly from the cellulose based solid matrix cards. The results in Table 4 show that the 2 TE washes produce the maximum number of colonies per punch but that an unprocessed punch also produces sufficient numbers of colonies of archival purposes. The lowest number of colonies was obtained using the full manufacturer's processing protocol, again indicating that DNA was being removed from the punch with the additional washing steps. Additional studies have shown that a punch washed just once in TE gives slightly more colonies than an unprocessed punch and slightly less than a punch washed twice in TE, and additional TE washes over two decrease the number of colonies obtained. While DNA amplification could not occur with an unprocessed punch, plasmid transformation can, although not as efficiently as with a minimally processed punch. This slight loss of efficiency can be explained by the loss in viability of some of the competent cells in a reaction with an unprocessed punch.

TABLE 4

| Punch Processing Protocol | Total Colonies per 2 mm Punch* |
|---|---|
| unprocessed | 137 |
| TE washes | 193 |
| full processing | 45 |

*average of three separate experiments

Example 3

To show the utility of FTA™ brand cellulose based solid matrix, over other similar collection devices for the archiving of plasmid DNA, an overnight culture of bacterial host cells (DH5α) containing the pSUsrmB2 plasmid were spotted onto FTA™ cards brand celulose based solid matrix or similar paper based collection devices and allowed to air-dry. The other collection devices used were: Isocode PCR DNA Sample Collection Device (Schleicher & Schuell, Keene, N.H.), Generation Capture Card Kit (Gentra Systems, Minneapolis, Minn.) and Whatman #4 filter paper (Clifton, N.J.). Whatman #4 filter paper has been used historically by researchers for short-term storage of live bacterial cells for applications such as transfer of a strain of bacteria between laboratories by mail or delivery service. Live bacterial cells can be recovered from the filter paper by placing a portion of the filter paper into a suitable culture medium for growth.

Punches (2 mm) were taken from each of these collection devices and the FTA™ brand cellulose based solid matrix, Isocode and Generation products were processed according to the manufacturer's directions and with the two abbreviated TE washes described above. The Isocode product is designed to release DNA from the paper, therefore both the processed punch as well as a one-tenth volume (5 ml) of the released DNA were tested. The Whatman #4 filter paper punches were not processed in any manner. The punches were then used in a transformation experiment using DH5α competent cells. In addition, a TE washed punch (or in the case of the Whatman #4 filter paper, an unprocessed punch) was placed into a control mock transformation containing 100 ml of SOC medium instead of 100 ml of competent cells to test that all the colonies obtained in the transformation experiments were derived from actual transformation events and not from carry-over of live bacteria.

The results in Table 5 show that the Gentra Generations product does not produce numbers of transformants in the same range as FTA™ brand cellulose based solid matrix paper. The Isocode product produced numbers of colonies in the same range as FTA™ paper brand cellulose based solid metrix, but only when the paper is processed first. The total number of colonies obtained will be influenced by copy number and size of the plasmid insert used. As expected, the Whatman #4 paper was an effective method for short-term storage of culturable bacterial cells shown by the equal numbers generated with and without competent cells, but not for long-term recovery of cells. Due to the nature of FTA™ Cards brand cellulose based solid matrix, the DNA stored on FTA™ paper brand cellulose based solid matrix is likely to be protected from damage for the long-term. Bacterial cells on FTA™ paper brand cellulose based solid matrix have shown no loss in transformation efficiency for at least 3 months. Blood stored on FTA™ paper brand cellulose based solid matrix, for more than 7 years has yielded DNA for PCR analysis.

to fluorescent automated sequencing using the ABI Prism Big Dye Terminator Cycle Sequencing Ready Reaction Kit (Cat. No. 4303149, PE Applied Biosystems, Foster City, Calif.) according to the manufacturer's directions and the resulting reactions were analyzed on the ABI Prism 377.

An excellent sequence was obtained from the M13 plaque that was directly transferred to the FTA™ Card brand cellulose based solid matrix. The read-length was greater than 600 nucleotides with no unreadable bases in the first 600 bases. When this sequence was compared to the known sequence of M13, there were 0 errors in the first 300 nucleotides and one error and one misread in the next 300 nucleotides (error rate 0.33% for 600 nucleotides). Sequence data generated from M13 infected cells on FTA™ Cards brand cellulose based solid matrix was readable, but less error-free indicating that sequence information can be obtained from this format, but optimization of cell concentration or processing methods may be required. M13 plaques placed directly on either Gentra Generations brand cards or Isocode brand cards also produced readable sequences.

The cellulose based solid matrix paper card is known for its utility in archiving, its ease of sample preparation, and elimination of potential biohazards in DNA from blood samples. According to the present invention, any matrix or solid medium (preferably a cellulose or paper based matrix and particularly FTA™ Cards brand cellulose based solid matrix) are also useful for archiving DNA from bacterial sources, both genomic and vectors. Thus, the invention represents a method for convenient and efficient storage, processing and recovery of vector or plasmid clones. This method could be very useful in storage of the vast numbers of subclones generated, for example, in large-scale genome sequencing projects.

TABLE 5

| | Total Number of Colonies per 2 mm Punch (pSUsrmB2 culture) | | | | |
|---|---|---|---|---|---|
| Processing Method | FTA ™* | Gentra Generation* | S&S Isocode | Whatman # 4 (10 days) | Whatman # 4 (25 days) |
| unprocessed | 137 | 2 | 5 | 247 | 0 |
| 2 TE | 193 | 5 | 170 | N.D. | N.D. |
| manufacturer's protocol | 45 | 0 | 15 | N.D. | N.D. |
| released DNA | N.D. | N.D. | 40 | N.D. | N.D. |
| mock transfection | 0 | 0 | 0 | 263 | 10 |

*FTA ™ and Gentra Generations data is the average of 3 separate experiments
N.D.: not determined

Example 4

Additional studies on the utility of cellulose based solid matrix paper with the M13 vector system were undertaken using FTA™ paper brand cellulose based solid matrix. M13 is a bacteriophage vector system that has the ability to produce single stranded DNA molecules that are particularly useful as DNA sequencing templates. However, preparation of purified templates is tedious and time-consuming. These cellulose based solid matrix cards were tested to see if they could simplify the purification of the sequencing template DNA. M13 plaques were either directly transferred to FTA™ paper brand cellulose based solid matrix or host DH5αF'IQ cells infected with M13 were applied to FTA™ paper brand cellulose based solid matrix and allowed to dry. Punches (2 mm) were taken from these cellulose based solid matrix cards and processed with TE (as these samples do not contain blood). After processing, the punches were subjected

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing one or more cells containing one or more vectors comprising:
   a) obtaining a solid matrix comprising one or more vectors; and
   b) contacting said matrix with one or more cells under conditions sufficient to allow said one or more vectors to be introduced into said one or more cells,
   wherein said solid matrix is a cellulose based matrix or a micromesh synthetic plastic matrix.

2. The method of claim 1, wherein said cells are prokaryotic cells.

3. The method of claim 2, wherein said prokaryotic cells are *Escherichia coli* cells.

4. The method of claim 1, wherein said matrix is contacted with said one or more cells in solution.

5. The method of claim 1, wherein said solid matrix further comprises:
   a. a weak base;
   b. a chelating agent; and
   c. an anionic surfactant or an anionic detergent.

6. The method of claim 5, wherein said matrix further comprises uric acid or a urate salt.

7. A method for producing one or more cells containing one or more vectors comprising:
   a) obtaining a solid matrix comprising one or more vectors; and
   b) contacting said matrix with one or more cells under conditions sufficient to allow said one or more vectors to be introduced into said one or more cells,
   wherein said solid matrix comprises a weak base, a chelating agent, and an anionic surfactant or an anionic detergent.

8. The method of claim 7, wherein said matrix further comprises uric acid or a urate salt.

9. The method of claim 7, wherein said cells are prokaryotic cells.

10. The method of claim 9, wherein said prokaryotic cells are *Escherichia coli* cells.

11. The method of claim 7, wherein said matrix is contacted with said one or more cells in solution.

12. A method for producing one or more cells containing one or more vectors comprising:
   a) obtaining a solid matrix comprising one or more vectors;
   b) contacting said matrix with a solution; and
   c) contacting said cells with said solution under conditions sufficient to allow said one or more vectors to be introduced into one or more cells,
   wherein said solid matrix is a cellulose based matrix or a micromesh synthetic plastic matrix.

13. The method of claim 12, wherein said cells are prokaryotic cells.

14. The method of claim 13, wherein said prokaryotic cells are *Escherichia coli* cells.

15. The method of claim 12, wherein said solid matrix further comprises:
   a. a weak base;
   b. a chelating agent; and
   c. an anionic surfactant or an anionic detergent.

16. The method of claim 15, wherein said matrix further comprises uric acid or a urate salt.

17. A method for producing one or more cells containing one or more vectors comprising:
   a) obtaining a solid matrix comprising one or more vectors;
   b) contacting said matrix with a solution; and
   c) contacting said cells with said solution under conditions sufficient to allow said one or more vectors to be introduced into one or more cells,
   wherein said solid matrix comprises a weak base, a chelating agent, and an anionic surfactant or an anionic detergent.

18. The method of claim 17, wherein said matrix further comprises uric acid or a urate salt.

19. The method of claim 17, wherein said cells are prokaryotic cells.

20. The method of claim 19, wherein said prokaryotic cells are *Escherichia coli* cells.

* * * * *

SEQUENCE LISTING

<160> NUMBER OF SEQ ID NOS: 7

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotides

<400> SEQUENCE: 1
gggaaagatt tatcggggat gggctgctgg cacgaagtta                    40

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: synthetic
      oligonucleotides

<400> SEQUENCE: 2
ctgagacacg gtccagactc ctacgtcacc gctacacctg ggattctacc         50

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: synthetic
      oligonucleotides

<400> SEQUENCE: 3
agagtttgat gatcctggct cagaaggagg tgatccagcc gca                43

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: synthetic
      oligonucleotides

<400> SEQUENCE: 4
cccagtcacg acgttgtaaa acgagcggat aacaatttca cacagg             46

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: synthetic
      oligonucleotides

<400> SEQUENCE: 5
gaataagtgc gacatcatca tcgtaaattt ctggcaaggt agac               44

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotides

<400> SEQUENCE: 6

```
-continued acttcttcgc ccccgttttc gctgacttga cgggacggcg                    40

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: synthetic
      oligonucleotides

<400> SEQUENCE: 7
gcgaggcata tttatggtga aggcatttcc gtgcaaaggt actaac          46
```